United States Patent [19]

Solazzo

[11] Patent Number: 4,776,848
[45] Date of Patent: Oct. 11, 1988

[54] URETHRAL FLUID APPLICATION DEVICE AND SYSTEM

[76] Inventor: Anthony Solazzo, 40 Wolf Hill Dr., Warren, N.J. 07060

[21] Appl. No.: 77,118

[22] Filed: Jul. 20, 1987

[51] Int. Cl.$^4$ .................. A61M 7/00; A61M 31/00
[52] U.S. Cl. ................................. 604/247; 604/54; 604/213; 604/275
[58] Field of Search ............ 604/27, 54, 171, 212–216, 604/275–276, 328

[56] References Cited

U.S. PATENT DOCUMENTS

| | | | |
|---|---|---|---|
| 885,999 | 4/1908 | Hoseason | 604/212 |
| 1,240,125 | 9/1917 | Doud | 604/328 |
| 1,669,601 | 5/1928 | Coon | 604/212 X |
| 3,421,509 | 1/1969 | Fioro | 604/171 |
| 4,183,358 | 1/1980 | Cohen | 604/328 |
| 4,650,474 | 3/1987 | DeBacker | 604/328 X |
| 4,692,154 | 9/1987 | Singery et al. | 604/172 |

FOREIGN PATENT DOCUMENTS 541574  7/1922  France .................... 604/215

Primary Examiner—Dalton L. Truluck

[57] ABSTRACT

The present invention involves a urethral fluid application device and system for insertion of fluids with backflow prevention. The device includes a tubular member having a feed port at one end and an outlet port at the opposite end, a unidirectional channel connecting the two ports and a one-way valve permitting flow only from the feed port to the outlet port. The device also includes a flange about the tubular member for contact with and attachment to the glans penis, as well as attachment means located on the flange. The system includes both the device and a supply container with a nozzle adapted to interconnect with the feed port of the device.

14 Claims, 1 Drawing Sheet

URETHRAL FLUID APPLICATION DEVICE AND SYSTEM

BACKGROUND OF THE INVENTION

1. Field of the Invention

The present invention is directed to a device and system for the application of a fluid into a male urethra. More particularly, the present invention is directed to such a device and system for inserting a fluid into a male urethra and preventing the fluid from backflowing out of the male urethra until desired.

2. Prior Art Statement

There is significant prior art on the concept of fluid flow into the human body and to unidirectional flow of fluids, but the art is lacking in devices and systems particular to the application of fluids to the male urethra.

Thus, U.S. Pat. No. 4,387,879, issued to Stefan Tauschinski, is directed to a self-sealing connector for use with plastic cannulas and vessel catheters. While it is a device to keep fluid into the body from backflowing, it is not applicable to the attachment to and use with a penis. Likewise, U.S. Pat. No. 4,346,704 to Lee K. Kulle, describes a sleeve valve for a parenteral solution device, capable of prevention of backflow but not applicable to penal application.

The one-way or unidirectional valve prior art is replete with variations for backflow prevention in tubes. Exemplary are early U.S. Pat. Nos. 274,447 and 555,588 which show squeeze valves flap valves.

SUMMARY OF THE INVENTION

The present invention involves a urethral fluid application device and system for insertion of fluids with backflow prevention. The device includes a tubular member having a feed port at one end and an outlet port at the opposite end, a unidirectional channel connecting the two ports and a one-way valve permitting flow only from the feed port to the outlet port. The device also includes a flange about the tubular member for contact with and attachment to the glans penis, as well as attachment means located on the flange. The system includes both the device and a supply container with a nozzle adapted to interconnect with the feed port of the device.

BRIEF DESCRIPTION OF THE DRAWINGS

The various embodiments and scope of the present invention will be more fully appreciated with the following detailed description when taken in conjunction with the accompanying drawings, in which.

DETAILED DESCRIPTION OF THE PRESENT INVENTION

Urologists dealing with the insertion of various fluids to the male urethra, for exploratory, diagnostic, non-surgical treatment or surgical purposes, frequently encounter backflow or oozing problems and unnecessary loss of such fluids. In the case of the application of a antibiotic or a topical anesthetic, it may be necessary to apply the fluid into the urethra and have it remain for a preset length of time, e.g. 20 minutes or the like. Backflow results in loss of fluid and sometimes loss of effectiveness of the fluid in the desired area.

Thus, in its broad sense, the primary object of the present invention is to allow for application of a fluid to the urethra while providing for the retention of the fluid for a desired period of time, e.g. to permit absorption. Thus, in the case of the application of a topical anesthetic for urological endoscopic procedures, it may be necessary to retain the anesthetic in the urethra for at least five to ten minutes for absorption of the anesthetic by mucosal surface prior to urological endoscopic procedures. This may effectively and efficiently be achieved by the device and system of the rresent invention.

Figure 1:
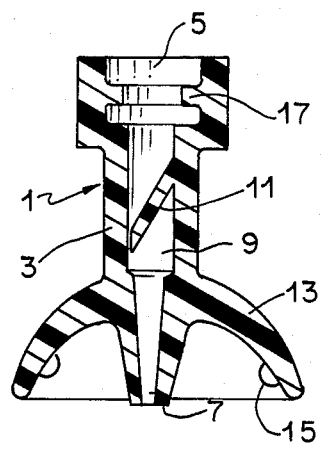
FIG. 1 illustrates a cut frontal plane view of one preferred embodiment of the device of the present invention.

Referring now to FIG. 1, there is shown a present invention urethral fluid application device 1 which includes tubular member 3. Feed port 5 is shown at the top of tubular member 3 and acts as an inlet into which the urethral fluid is sent. Outlet port 7 is at the opposite end as shown and has a tapered external feature to enhance insertion. Outlet port 7 is inserted into the urethra and acts as an outlet for the outflow of the urethral fluid from the device 1 into the urethra (not shown here; discussed with FIG. 3 below).

There is a channel 9 which is designed as unidirectional (no side ports or diversions) located within tubular member 3 and contains one-way valve 11. In this case, the one-way valve 11 is a simple flap valve which yields to fluid flowing down channel 9 from feed port 5 to outlet port 7 but closes upon backflow and prevents fluid from exiting the device 1 at the feed port 5. It should be noted that the one-way valve may be a split flap or squeeze valve or a float or ball valve. The particular valve is a matter of choice and are exemplified by those shown in the cited prior art.

Device 1 also includes a flange 13 which surrounds (at least in part) the tubular member 3 and is adapted to contact the glans penis and prevent insertion of device 1 beyond the underside of flange 3 into the urethra. Glans penis attachment means 15 is shown, and, in this embodiment, is adhesive (in the form of a single annular strip or a series of adhesive spots, such as the adhesive used for plastic bandage strips. Other glans penis attachment means may be utilized, such as, bandage over the flange and extending beyond the flange for taping to the glans penis. Other means, such as, non-adhesive means may be used, such as the flexible band described in conjunction with FIG. 2 below.

Optional fluid container attachment thread 17 is shown in FIG. 1 and may be used as a snap-in or a screw-in mechanism for gel, cream or other tube or container attachment. Alternatively, thread 17 could be eliminated for use without direct connection to a tube, e.g. for use by simple insertion.

Figure 2:
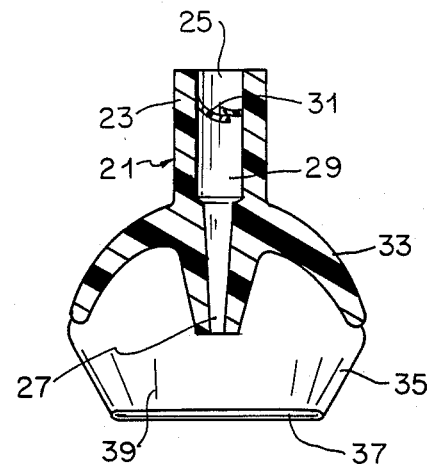
FIG. 2 shows a cut frontal plane view of another preferred embodiment of the present invention; and, FIG. 3 sets forth a preferred system of the present invention including a portion of a fluid supply, a present invention device and a portion of a glans penis.

As shown in FIG. 2, is a present invention device 21 is shown having a tubular member 23, feed port 25, outlet port 27, unidirectional channel 29 and one-way valve 31. In this embodiment one-way valves 31 is a two piece squeeze valve which is normally biased closed due to its structure, as shown, but may be pushed open like one-way double doors, by force of inserting fluid into feed port 25 or may be opened by being manually squeezed at its location (provided that tubular member 23 is constructed of thin enough material, e.g. plastic, to be at least partially flexible). In any event, the one-way valve 31 remains closed when any backflow occurs against it up from outlet port 27 toward feed port 25 and such flow is, therefore, contained.

Also shown in FIG. 2 is flange 33 and glans penis attachment means 39 which includes flexible sheath 35 and expandable band 37. The flexible sheath 35 may be completely circumferential or may be partial and may itself be stretchable or non-stretchable. The objective is to have a sheath 35 which may fit over the glans penis to allow the expandable band 37 to securely affix the device to the penis during use with insertion of the outlet port 27 into the urethra. Alternatives to the sheath 35 may now be apparent, e.g. the use of an elastic netting, without exceeding the scope of the present invention.

In general, a critical feature of the present invention involves the aforesaid described flange to limit the depth of insertion so as to leave part of the tubular member exposed for application of desired fluid(s) and to create an aspect of the device to enhance attachment. In this regard, an additional feature which is critical is the glans penis attachment means, without which the prevention of backflow might not otherwise be successful. The flange shown is preferred but other configurations such as an open frame, star or other shape could be used. Arcs or spoke-like members as well as other configurations could be used and likewise not exceed the scope of the meaning of "flange" as used herein. Thus, the flange may be any protrusion radially extending from the tubular member which performs the twofold purpose of limiting insertion depth and allowing for attachment.

The term "tubular member" may be taken to include any piece or pieces of material having a greater length to width dimension and being hollow lengthwise, and may have a circular, rectangular or other cross-section (internally or externally, although circular externally is preferred to conform to the material shaping of the urethra). It may be constructed of plastic, rubber, ceramic, metal or the like and should be free of sharp edges, at least on the outlet port end. Also, it may be tapered or conical to enhance insertion. It may be flexible, semi-flexible or rigid and is preferably semi-flexible or rigid. It is also disposable in its preferred embodiment and may be constructed of plastics conventionally used in intravenous connectors, etc. which are known.

The "fluid" which is being applied to the urethra may be liquid, sol, gel, cream, paste or other material with low or high viscosity and need only be flowable. It may be anesthetic, antibiotic, antiflammatory, a cleaning solution, a preparatory fluid, a placebs, or any other fluid which a doctor, nurse, urologist or other treating professional may desire to apply to a urethra for a period of time.

Figure 3:
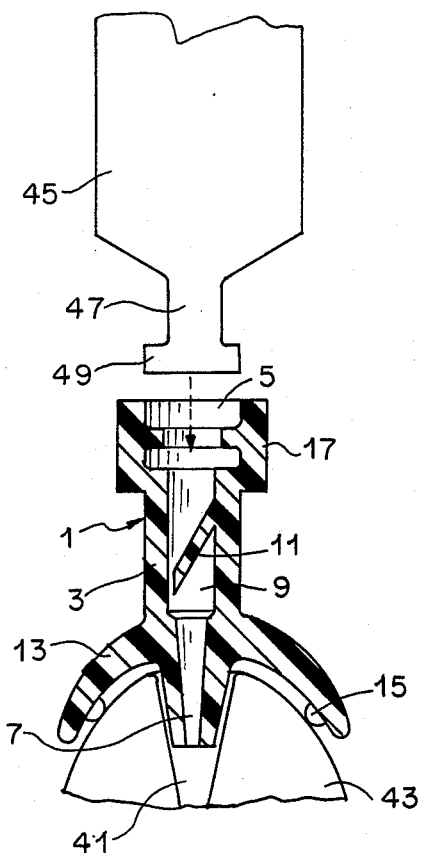

Referring now to FIG. 3, one embodiment of the present invention *system* is shown which includes both device and fluid container 45. Device 1 is that which is shown in FIG. 1 and like parts are like numbered. Fluid container 45 has an outlet neck 47 which is adapted to snap into the feed port 5 and become connected thereto in a secure fashion via lip 49, which snaps into feed port 5 such that lip 49 is held in place by single thread 17. The flange 13 is attached to glans penis 43 by adhesive 15, and outlet port 7 of device 1 is inserted into urethra 41 as shown. Fluid within container 45 may now be squeezed into device 1 through channel 9, past valve 11, down outlet port 7 and into urethra 41. A slight increase in intraurethral pressure creates a tendency for the fluid to be exited but retention is achieved because valve 11 closed to prevent backflow. The container 45 may be a small, disposable tube and may be left attached or removed. Once the fluid has had contact with the urethra 47 for at least some minimum desired time period, the device 1 may be removed and discarded.

Obviously, numerous modifications and variations of the present invention are possible in light of the above teachings. It is therefore understood that within the scope of the appended claims, the invention may be practiced otherwise than as specifically described herein.

What is claimed is:

1. A urethral fluid application device for inserting a fluid into a male uretha and for preventing the fluid from backflowing out of the mate urethra, which comprises:
a tubular member for partial insertion into a male urethra, which includes:
(a) a feed port at one end of said tubular member;
(b) an outlet port at the opposite end of said tubular member having a maximum outside dimension to permit insertion into a male urethra;
(c) a unidirectional fluid flow channel within said tubular member running from said feed port in a direction toward and to said outlet port;
(d) a one-way valve located within said channel permitting flow only from said feed port to said outlet port;
(e) a flange located on the outside of said tubular member adapted to contact a glans penis for attachment thereto and to prevent further insertion of the outlet port end of said tubular member into a male urethra; and,
(f) glans penis attachment means located on said flange for attachment of said device to a glans penis while the outlet port end of said tubular member is inserted in a male urethra.

2. The device of claim 1 wherein said outlet port has a tapered exterior to enhance insertion into the urethra.

3. The device of claim 1 wherein said valve is a one-way flap valve.

4. The device of claim 1 wherein said glans penis attachment means includes adhesive.

5. The device of claim 4 wherein said adhesive is located directly on the underside of said flange.

6. The device of claim 4 wherein said adhesive is located on adhesive tape attachable to said flange.

7. The device of claim 1 wherein said glans penis attachment means involves non-adhesive attachment by expandable band.

8. A system for applying urethral fluid to the male urethra which includes:
(I) a fluid container having urethral fluid therein and having an outlet neck adapted to be attached to a feed port of a urethral fluid application device; and,
(II) a urethral fluid application device, including:
(a) a feed port at one end of said tubular member;
(b) an outlet port at the opposite end of said tubular member having a maximum outside dimension to permit insertion into a male urethra;
(c) a unidirectional fluid flow channel within said tubular member running from said feed port in a direction toward and to said outlet port;
(d) a one-way valve located within said channel permitting flow only from said feed port to said outlet port;

(e) a flange located on the outside of said tubular member adapted to contact a glans penis for attachment thereto and to prevent further insertion of the outlet port end of said tubular member into a male urethra; and, (f) glans penis attachment means located on said flange for attachment of said device to a glans penis while the outlet port end of said tubular member is inserted in a male urethra.

9. The system of claim 8 wherein said outlet port has a tapered exterior to enhance insertion into the urethra.

10. The system of claim 8 wherein said valve is a one-way flap valve.

11. The system of claim 8 wherein said glans penis attachment means includes adhesive.

12. The system of claim 11 wherein said adhesive is located directly on the underside of said flange.

13. The system of claim 11 wherein said adhesive is located on adhesive tape attachable to said flange.

14. The system of claim 8 wherein said glans penis attachment means involves non-adhesive attachment by expandable band.

* * * * *